United States Patent
Engelbrecht

(10) Patent No.: US 6,852,774 B1
(45) Date of Patent: Feb. 8, 2005

(54) ADHESIVE SYSTEM FOR SILICONES

(75) Inventor: Jürgen Engelbrecht, Elmshorn (DE)

(73) Assignee: S & C Polymer Silicon- und Composite- Spezialitaten GmbH, Elmshorn (DE)

( * ) Notice: Subject to any disclaimer, the term of this patent is extended or adjusted under 35 U.S.C. 154(b) by 0 days.

(21) Appl. No.: 09/455,651

(22) Filed: Dec. 7, 1999

(30) Foreign Application Priority Data

Apr. 9, 1999 (DE) .......................................... 199 16 131

(51) Int. Cl.$^7$ ............................................... A61K 6/10
(52) U.S. Cl. ................................................. 523/109
(58) Field of Search ......................................... 523/109

(56) References Cited

U.S. PATENT DOCUMENTS

| | | | | | |
|---|---|---|---|---|---|
| 4,107,845 A | * | 8/1978 | Lee | ............................... | 32/15 |
| 4,264,489 A | * | 4/1981 | Ibsen | ....................... | 260/42.52 |
| 4,657,959 A | * | 4/1987 | Bryan | .......................... | 524/266 |
| 4,748,198 A | * | 5/1988 | Takahashi | .................... | 524/273 |
| 5,278,201 A | * | 1/1994 | Dunn | .......................... | 523/113 |
| 5,374,664 A | * | 12/1994 | Zalsman | ...................... | 523/118 |
| 5,709,548 A | * | 1/1998 | Oxman | ........................ | 433/218 |
| 5,769,633 A | * | 6/1998 | Jacobs | .......................... | 433/37 |
| 6,031,016 A | * | 2/2000 | Ibsen | ........................... | 522/79 |
| 6,482,871 B1 | * | 11/2002 | Aasen et al. | ................. | 523/116 |

* cited by examiner

Primary Examiner—Edward J. Cain
(74) Attorney, Agent, or Firm—Frommer Lawrence & Haug LLP; Ronald R. Santucci

(57) ABSTRACT

The present invention relates to a kit of parts, comprising at least one partially resoluble (co) polymer, at least one adhesive for silicones, optionally a base body, and optionally a silicone composition. Moreover, the invention is the use of parts in a kit for the manufacture of an impression tray.

24 Claims, No Drawings

ADHESIVE SYSTEM FOR SILICONES

TECHNICAL FIELD

The present invention relates to a kit which has a) at least one partially resoluble (co-) polymer, b) at least one adhesive for silicones, c) optionally a base body, and d) optionally a silicone composition. The instant invention also relates to a method of manufacturing a molding using the parts in the aforementioned kit.

BACKGROUND OF THE INVENTION

Impressions using impression compositions especially in the field of dentistry often require the use of so-called individually formed impression trays. Individual impression trays are individually manufactured moldings in the form of an impression tray, which are manufactured, for example, from self-curing mixtures of methyl methacrylate/ polymethyl methacrylate or from photo-curable composite plates (consisting of multifunctional photo-curable (meth-) acrylate mixtures to which glass powder has been added), in dental applications called "photo-curable individual impression tray plates."

Silicones are usually used as impression compositions in the field of dentistry. The bond between the impression trays and silicones poses a problem, however: silicones do not by themselves adhere to plastics or composites. Nonetheless, in order to provide adhesion between silicone impression compositions and impression trays, attempts were firstly made to anchor the impression compositions stably in the impression tray, and to prevent them from lifting out of the impression tray after the impression has been taken, with the aid of mechanical retaining means, such as holes, undercuts, bent-round rims, etc., that is to say by purely mechanical means.

Attempts were also made to improve the adhesion of the silicone compositions to impression trays by molecular/ mechanical means with the aid of solutions of viscous silicone polymers. Generally such silicone impression tray adhesives are solutions of only partially crosslinked silicones in volatile solvents. Since no direct chemical bonding occurs between the silicone impression composition and the partially crosslinked silicone polymers of the impression tray adhesive, those adhesives can be used both for silicone impression compositions that are crosslinked by condensation and for those crosslinked by addition.

Both above-mentioned measures for better adhesion of the silicone impression compositions to the impression trays, however, provide unsatisfactory solutions: it is especially difficult to introduce mechanical retaining means into individually manufactured impression trays since they must be produced, for example, subsequently by boring. In the case of such rigid trays, boring also easily results in stress cracks; in addition, too many mechanical retaining holes weaken the impression trays' breaking strength and resistance to bending.

The commercially available solvent-containing viscous adhesives have only an auxiliary adhesive action: in the case of relatively strong tensile forces on removal of the impression from the object of which the impression is to be taken, such as a tooth, the silicone impression lifts up from the impression tray and becomes deformed and the viscous adhesive comes away with many drawn-out threads being formed. The deformation of the impression easily results in defective fittings.

It has been known for a short time that adhesives that are used to bind non-hardening silicone re-lining materials securely to plastics for prostheses (e.g. accompanying Patent Application DE 199 05 224.7, Patent Application DE 196 35 696 A1 or Patent Specification EP 0 632 063 A1) also adhere excellently to impression trays that are slightly partially soluble. Partially soluble trays are, for example, trays made of polystyrene, polycarbonate, on monomer/polymer-based individual impression trays, such as, for example, those made of methyl methacrylate/polymethyl methacrylate, such adhesives can result in good adhesion of the silicone impression composition to precisely that type of individual impression trays.

It is problematic, however, to produce good adhesion of silicones to the surface of crosslinked methacrylates, especially to individual photo-curable impression trays based on a methacrylate composite, which are used in large numbers. The mentioned new adhesion primers for silicones fail on those types of polymerized kits.

SUMMARY OF THE INVENTION

The problem underlying the invention was therefore to provide a kit of parts that enables a reliable easy-to-produce bond between impression trays, such as impression trays consisting of methacrylate composites and especially special photo-curable individual impression trays, and silicone compositions, the bond being approximately as strong as the cohesion of the silicone composition itself.

DETAILED DESCRIPTION OF THE INVENTION

According to the invention the problem is solved by a kit of parts comprising a) at least one partially resoluble (co-) polymer, b) at least one adhesive for silicones, c) optionally a base body, and d) optionally a silicone composition.

According to the invention, the base body may comprise or consist of polymers or copolymers of methacrylates. It may be a composite body and may additionally comprise fillers, such as glass power.

The optionally comprised base body may be an impression tray, especially an individually manufactured impression tray and more especially an individually manufactured photo-curing impression tray. The base body may also be a dental crown or bridge or a temporary crown or bridge.

The soluble or partially (re-)soluble (co-)polymers may be or comprise, for example, polystyrene, polycarbonate, poly (meth-)acrylate, polyvinyl, polysulphone, polymethylpentene or polystyrene acrylonitrile or mixtures thereof, the poly(meth-)acrylates preferably being polymers or mixed polymerisates of methyl, ethyl, propyl, butyl, neopentyl or tetrahydrofurfuryl esters of acrylic acids or methacrylic acids, on account of their being chemically related to the crosslinked methacrylates.

In principle, however, any soluble or partially (re-)soluble polymer is suitable that can bond with sufficient strength to (co-)polymerized base bodies, especially based on dimethacrylates or other multifunctional methacrylates to which fillers have been added or containing no fillers. A bond is sufficiently strong when it has an adhesive strength of at least 50%, more especially of at least 90% and most especially of at least 100% of the cohesive strength of the impression composition used.

The adhesive for silicones may be a (co-)polymer or a mixture of (co-)polymers containing SiH or vinyl groups; it is especially preferred for the (co-)polymer or the mixture of (co-)polymers to contain at least one SiH or vinyl group per unit, each unit corresponding to two originally used monomers. Such adhesives are disclosed in the accompanying specification DE 199 05 224.7, to which reference is expressly made in respect of this disclosure.

Alternatively, the adhesive for silicones may be a (co-)polymer or a mixture of (co-)polymers containing silanol groups

wherein X=OH, —O—R$_c$ or radicals of the formulae —O—CO—R$_c$, —NR$_d$—R$_c$, —NR$_d$—CO—R$_c$, and the moieties R$_c$ and R$_d$ or the free bonds at the Si atom each independently of the others may be H atoms, OH groups, alkyl groups, alkoxy groups or aryl groups. It is especially preferred for the radicals of formulae —O—R$_c$, —O—CO—R$_c$, —NR$_d$—R$_c$, —NR$_d$—CO—R$_c$ to be readily hydrolysable radicals. Such groups of formula X are also disclosed in the accompanying Patent Application "Adhesion promoters for silicone materials", Attorney Ref. No. 9817, filed at the German Patent and Trade Mark office on Jul. 4, 1999, to which reference is also expressly made in respect of this disclosure.

According to a preferred embodiment, the partially resoluble (co-)polymers and/or the adhesives for silicones are dissolved or partially dissolved in at least one readily volatile inert solvent. An aliphatic or aromatic, halogenated or non-halogenated hydrocarbon, ether, ketone, ester or cyclic siloxane may be used as solvent.

The silicone composition d) may be, for example, a silicone impression composition for taking impressions of teeth.

In the kit of parts according to the invention, components a), b), optionally c) and optionally d) can be separated, for example they may be present in separate containers, such as bottles or cans. The base body may also be packed separately in a different manner.

By means of such adhesive systems for silicone compositions, especially for adhesion to composite moldings, an intimate bond is produced between the silicone composition and the composite moldings.

According to the invention there is also provided a method of manufacturing a molding, such as an impression tray, in which a) a solution of at least one partially resoluble (co-) polymer is applied to at least one surface of a base body, b) the partially resoluble (co-)polymer(s) is/are dried, c) a solution of at least one adhesive for silicones is applied to the layer of the partially resoluble (co-) polymer(s), d) the adhesive(s) for silicones is/are dried, and e) optionally a silicone composition is applied to the adhesive(s)

That method can be carried out, for example, by a dentist, a dental technician or a dental assistant, moreover, according to the invention an impression tray is provided which can be manufactured according to the method described above.

The partially resoluble (co-)polymers used in step a) and/or the adhesives for silicones used in step c) are, according to a preferred embodiment, dissolved in at least one of the above-mentioned readily volatile inert solvents.

An impression tray according to the invention having improved adhesion of silicone compositions to composite moldings, especially a corresponding individual photocured impression tray, can be manufactured especially as follows:

1. solutions of partially resoluble polymers applied to the composite surface and dried so that they adhere to that composite surface; and
2. adhesive solutions for curable silicones are applied to the layer of the partially resoluble polymers and dried so that they adhere to the partially resoluble polymer surfaces, so enabling an intimate bond between a silicone composition that is to be applied and the partially soluble polymer surface.

For example, individual impression trays can be used according to the invention. Individual impression trays, which may also comprise dimethacrylates to which fillers have been added, are generally initially in the form of prefabricated photo-curable plates and are shaped on a plaster model to form an individual impression tray and are photo-cured. After removal of the oxygen-inhibiting lubricating layer with ethanol, according to the invention, for example, a thin film of a partially soluble polymer is applied to the surface of the individual impression tray. This is effected easily by applying the polymer dissolved in readily volatile inert solvents.

As described above, base bodies, such as methacrylate base bodies, that have been treated with partially soluble polymers are treated according to the invention in a second step with silicone adhesion promoters (primers), as described, for example, in the accompanying Patent Application DE 199 05 224.7 or in Patent Application DE 196 35 696 A1 or in Patent Specification EP 0 632 060 A1 for addition-crosslinking systems (A), or as also described, for example, in the accompanying Patent Application "Adhesion promoters for silicone materials", Attorney Ref. No. 9817, filed at the German Patent and Trade Mark Office on Jul. 4, 1999, for condensation-crosslinking systems (C).

Suitable primers (A) for coating base bodies, especially individual photo-cured impression trays, with addition-crosslinking impression compositions may be solutions of adhesive polymers that comprise a sufficient amount of SiH or vinyl groups and that can dissolve adequately in the applied polymer surface of the dimethacrylate base body, sufficiently volatile solvents being used. Impression trays treated in that manner are ready and suitable for strong adhesion of addition-crosslinking silicones.

Suitable primers (C) for coating impression trays with condensation-crosslinking impression compositions may be, for example, solutions of polymers comprising a sufficient amount of silanol groups

wherein X=OH, —O—R$_c$, —O—CO—R$_c$, —NR$_d$—R$_c$, —NR$_d$—CO—R$_c$, and the moieties R$_c$ and R$_d$ are as defined above, the solutions of the polymers being able to dissolve adequately in the applied polymer surface (1st layer) of the dimethacrylate impression tray and the solvents used being sufficiently volatile. Impression trays treated in that manner are ready and suitable for strong adhesion of condensation-crosslinking silicones to that surface.

The kit of parts and impression tray according to the invention can be used for medical applications, especially for dental applications, their use as impression trays for silicone compositions being especially preferred. The impression compositions used are, for example, silicone compositions for taking impressions of teeth.

In the case of individual impression trays, the trays prepared in that manner can be charged directly with impression composition of the appropriate curing type at the dentist's and inserted into the mouth in order for the impression to be taken. On removal of the charged impression tray, the impression composition and the impression tray remain securely bonded. Portions of the cured impression composition do not become detached from the impression tray, and corresponding distortions and defective impressions do not occur. Attempts to remove the impression composition from the impression tray result in impression material breaking away.

Many other applications of bonding silicones to crosslinked methacrylate plastics are conceivable and in line with the invention.

For example, with the aid of the adhesive system according to the invention flexible silicone gum masks can be secured at the lower edge of composite-lined dimethacrylate-based dental crowns or bridges or temporary crowns or bridges in order to cover up insufficient gingival margins.

Moreover, where patients have contact allergies to contents of composites, the composites can be coated according to procedure of the patent with a thin layer of curing silicone, or composite moldings in industrial applications can be coated in a manner according to the patent and flexibly bonded lastingly with a silicone adhesive.

EXAMPLES

Adhesion of an addition-crosslinking silicone impression composition to a photo-curable individual impression tray A photo-curable impression tray plate (Megatray, made by Megadenta, Germany) is shaped on a plaster model to form an impression tray and is photo-cured for 3 minutes in an irradiation unit (Megaflash, made by Megadenta). The oxygen-inhibiting layer on the surface is removed from the inner face of the resulting impression tray by means of an alcohol-impregnated cloth.

A 15% solution of a soluble polymer powder (polymethyl methacrylate MW332, made by Röhm, Germany) in toluene is prepared and this is applied thinly to the cleaned inner face of the impression tray and is left to dry.

The silicone adhesion primer corresponding to Example 2 of the accompanying Patent Application DE 199 05 224.7 is then applied to the so treated inner face and is dried. The impression tray is then loaded with the addition-crosslinking silicone pre-impression composition R-si-line putty (R-Dental, Germany) and an impression is taken in the mouth of the teeth of an upper jaw. After curing, the impression tray with the cured impression composition is removed without a trace of the silicone becoming detached from the inner face of the impression tray. The impression composition is bonded securely to the impression tray and can be removed only by destroying the impression composition.

I claim:

1. A kit for bonding silicone compositions to a base surface made from polymers, polymers of methacrylates or fillers with said surface being part of a structure which includes an impression tray, dental crown, bridge, temporary crown or temporary bridge, comprising:
    a) at least one partially re-soluble (co-)polymer adapted to form a first layer on said base surface; and
    b) at least one adhesive for silicone adapted to form a second layer in an overlying relationship to said first layer, wherein the adhesive for silicones is a (co-)polymer or a mixture of (co-)polymers containing at least one SiH, vinyl groups or silanol groups.

2. The kit according to claim 1 further comprising a base body.

3. The kit according to claim 2 further comprising a silicone composition.

4. The kit according to claim 2 wherein the base body comprises polymers or copolymers of methacrylates.

5. The kit according to claim 2 wherein the base body additionally comprises fillers, such as glass powder.

6. The kit according to claim 2 wherein the base body is an impression tray, a dental crown, bridge, temporary crown, or a temporary bridge.

7. The kit according to claim 1 whrein the partially resoluble (co-)polymers comprise polystyrene, polycarbonate, poly(meth-)acrylate, polyvinyl chloride, polysulphone, polymethylpentene, polystyrene acrylonitrile or mixtures thereof.

8. The kit according to claim 7 wherein the poly(meth-)acrylates comprise polymers or mixed polymerisates of methyl, ethyl, propyl, butyl, neopentyl or tetrahydrofurfuryl esters of acrylic acids or methacrylic acids.

9. The kit according to claim 1 wherein the partially resoluable (co-) polymers and/or the adhesives for silicones are dissolved or partially dissolved in at least one readily volatile inert solvent.

10. The kit according to claim 9 wherein the solvent is an aliphatic or aromatic, halogenated or non-halogenated hydrocarbon, ether, ketone, ester, or cyclic siloxane.

11. The kit according to claim 3 wherein the silicone composition comprises a silicone impression composition for taking impressions of teeth.

12. The kit according to claim 1 wherein components a) and b) are present in separate containers.

13. The kit according to claim 2 wherein components a), b), and c) are present in separate containers.

14. The kit according to claim 3 wherein components a), b), c), and d) are present in separate containers.

15. A method of manufacturing a molding, comprising the steps of:
    a) applying a solution of at least one partially resoluble (co-)polymer to at least one surface of composite;
    b) drying the partially resoluble (co-)polymer(s);
    c) applying a solution of at least one adhesive for silicones to the layer of the partially resoluble (co-)polymer(s); and
    d) drying the adhesive(s).

16. The method of manufacturing a molding according to claim 15 further comprising applying a silicone composition to the adhesive(s).

17. The method of manufacturing a molding according to claim 15 wherein the partially resoluble (co-)polymer and/or adhesive for silicones ar dissolved in at least one solvent.

18. The method of manufacturing a molding according to claim 17 wherein the solvent is a readily volatile inert solvent.

19. The method of manufacturing a molding according to claim 18 wherein the partially resoluble (co-)polymers comprise polystyrene, polycarbonate, poly(meth-)acrylate, polyvinyl chloride, polysulphone, polymethylpentene, polystyrene acrylonitrile or mixtures thereof.

20. The method of manufacturing a molding according to claim 19 wherein the poly(meth-)acrylates comprise polymers or mixed polymerisates of methyl, ethyl, propyl, butyl, neopentyl or tetrahydrofurfuryl esters of acrylic acids or methacrylic acids.

21. The method of manufacturing a molding according to claim 15 wherein the adhesive for silicones is a (co-)polymer or a mixture of (co-)polymers comprise at least one SiH, vinyl group or silanol group.

22. The kit according to claim 1, wherein the base surface is used for manufacturing a molding or an impression tray for silicone compositions.

23. A molding produced according to the process of claim 15.

24. A molding produced according to the process of claim 16.

* * * * *